United States Patent [19]
Konno et al.

[11] Patent Number: 4,465,507
[45] Date of Patent: Aug. 14, 1984

[54] HERBICIDAL ACETANILIDES

[75] Inventors: Kazuhiko Konno, Ami; Atsushi Goh, Ushiku; Yoshihiro Usui; Kaoru Ikeda, both of Ami, all of Japan

[73] Assignee: Mitsubishi Petrochemical Co., Ltd., Tokyo, Japan

[21] Appl. No.: 366,422

[22] Filed: Apr. 7, 1982

[30] Foreign Application Priority Data

Apr. 15, 1981 [JP] Japan ................................. 56-55624

[51] Int. Cl.³ .................... A01N 31/00; A01N 37/18; A01N 37/38; A01N 37/34
[52] U.S. Cl. ......................................... 71/98; 71/118; 71/105; 71/106; 71/113; 71/103; 71/116; 71/108; 71/100; 564/175; 564/158; 564/36; 260/453 RW; 260/500.5 H; 260/465 E; 260/465 F
[58] Field of Search ................ 260/500.5 H, 453 RW, 260/465 E, 465 F; 564/36, 175, 158; 71/100, 118, 105, 106, 113, 98, 103, 116, 108

[56] References Cited

U.S. PATENT DOCUMENTS 4,191,554  3/1980  Gregory ...................... 260/453 RW

OTHER PUBLICATIONS

Nolles, Textbook of Organic Chemistry, 2nd Ed., W. B. Saunders Company, Philadelphia, 1958, p. 189.

Primary Examiner—Henry R. Jiles
Assistant Examiner—Robert C. Whittenbaugh
Attorney, Agent, or Firm—Wenderoth, Lind & Ponack

[57] ABSTRACT

A tri- or tetra-substituted phenoxy alkylene- or alkenylene-anilide compound represented by the following formula

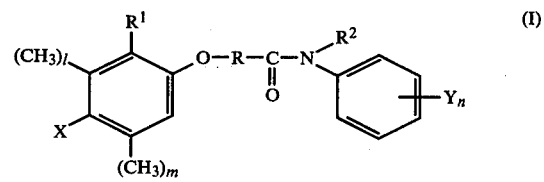

wherein R, $R^1$, $R^2$, X, Y, l, m and n are as defined in claim 1; a process for producing the aforesaid anilide compound; and its use as a herbicidal composition.

10 Claims, No Drawings

HERBICIDAL ACETANILIDES

This invention relates to a tri- or tetra-substituted phenoxy alkylene- or alkenylene-anilide compound not described in the prior literature and the use of said compound for controlling the growth of undesired vegetation.

More specifically, the invention pertains to a tri- or tetra-substituted phenoxy alkylene- or alkenylene-anilide compound represented by the following formula

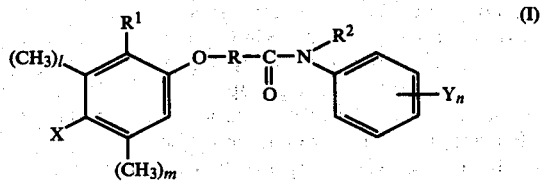

wherein
R represents a linear or branched lower alkylene or alkenylene group,
$R^1$ represents a methyl group or a halogen atom,
$R^2$ represents a hydrogen atom, or a lower alkyl, lower alkoxy or hydroxyl group,
X represents a halogen atom,
Y represents a member selected from the class consisting of lower alkyl groups, halogenated lower alkyl groups, lower alkoxy groups, halogen atoms, a nitro group, a cyano group, a hydroxyl group, an amino group, lower alkylamino groups, lower alkanoyloxy groups, lower alkanoylamino groups, lower alkylthio groups, lower alkylsulfonyl groups, lower alkanoyl groups, a carboxyl group, lower alkoxycarbonyl groups and lower alkylaminocarbonyl groups,
l and m are each 0 or 1 provided that l and m are not zero at the same time, and
n is 0 or an integer of 1 to 4 and when n is an interger of 2 to 4, a plurality of Y's are identical or different.

This invention also relates to a process for producing the aforesaid novel anilide compound; a composition containing the novel anilide compound as an active ingredient; a method for controlling weeds by applying an effective amount of the novel anilide compound to the locus to be protected from the weeds, for example the locus where undesired vegetation is growing or is to grow; and the use of the compound of formula (I) in combination with another herbicidally active compound, a composition comprising both, and a method for applying both for controlling undesired vegetation.

Many phenoxycarboxylic acid-type herbicidal compounds have previously been known, and for example 2,4-dichlorophenoxyacetic acid [2,4-D], 2-methyl-4-chlorophenoxyacetic acid [MCP] and γ-(2-methyl-4-chlorophenoxy)butyric acid have actually been used for practical purposes. These phenoxycarboxylic acid-type herbicidal compounds commonly have the defect that they have phytotoxicity to crops of the family Gramineae, especially to their roots. This constitutes a limitation to their widespread practical application.

On theother hand, N,N-dimethyl-2-(2,4-dichloro-5-methyl-phenoxy) acetoamide (British Pat. No. 823,208) and 2,4-dichloro-5-methyl-dimethylamide (German OLS No. 1949289) are known as phenoxycarboxylic amide-type herbicidal compounds. These compounds, however, have the defect of weak herbicidal activity against broad-leaved weeds, and show no plant hormonal action.

In order to remove such a limitation or defect, many proposals have been made about phenoxycarboxylic acid anilide-type herbicidally active compounds and compositions containing them. But none of them have proved to be entirely satisfactory. Such proposals have been made, for example, in Japanese Patent Publication No. 15122/1964 (Chem. Abstracts, vol. 62, 7686f), Japanese Patent Publication No. 18734/1965 (Chem. Abstracts, vol. 64, 12603b), Japanese Laid-Open Patent Publication No. 120123/1977, Japanese Laid-Open Patent Publication No. 96323/1978, British Pat. No. 1,041,982, Chem. Abstracts, vol. 71, 2433h, Chem. Abstracts, vol. 45, 10218i, Chem. Abstracts, vol. 55, 4355h, and J. Chem. Soc., p. 2335 (1961). None of these literature references describe general compounds which can include the active compound of the present invention represented by general formula (I).

Japanese Patent Publication No. 40731/1973 proposed a mixed paddy herbicide comprising 2,6-di-tert-butyl-4-methylphenyl-N-methylcarbamate [DBTC] and a phenoxy fatty acid-type compound. In this proposal, the general formula of the phenoxy fatty acid compound shows that the benzene ring of the phenoxy group may have two or more chlorine atoms and/or methyl groups. The only example of the tri-substituted derivative shown therein is 2,4,5-tri-chlorophenoxyacetic acid, and this patent document does not specifically disclose tri- or tetra-substituted phenoxy carboxylic acid anilide derivatives. The sole phenoxycarboxylic acid anilide compounds is an ortho-chloroanilide derivative of MCP [MCPCA].

The present inventors have continued to study the relation of phenoxycarboxylic acid anilide-type herbicidally active derivatives to their herbicidal activity and phytotoxicity to plants of the family Gramineae. This work led to the discovery that the type of substituents on the benzene ring of the phenoxy group of the phenoxycarboxylic acid anilide derivatives and the mode of their substitution have an important bearing on the herbicidal activity, phytotoxicity to gramineous crops and other characteristics of these derivatives.

Further investigations have led to the discovery that novel compounds of formula (1) which contain 3 to 4 in total of both halogen atoms and methyl groups on the benzene ring in such a way that they are 2-methyl or halo substituted, or 3- and/or 5-methyl and 4-halo substituted can be easily synthesized, and that the compounds of formula (1) have excellent herbicidal activity, low phytotoxicity, excellent selectivity between weeds and gramineous crops, a prolonged residual effect, a broadened range of the suitable period of application, etc.

Investigations of the present inventors have shown that anilide-type herbicidal compounds, for example the aforesaid 2,4-D and MCP-type compounds proposed in Japanese Patent Publication No. 15122/1964 (Chem. Abstracts, vol. 62, 7686f), Japanese Patent Publication No. 18734/1965 (Chem. Abstracts, vol. 64, 12603b), British Pat. No. 1,041,982 and Chem. Abstracts, vol. 71, 2433h, give rise to a problem of phytotoxicity to gramineous crops, and cause higher phytotoxicity when their herbicidal activity is higher; and that on the other hand, phenoxycarboxylic acid anilide-type herbicidally active derivatives such as those proposed in the above-cited Japanese Laid-Open Patent Publications Nos.

120123/1977 and 96323/1978 generally have lower phytotoxicity than the anilide-type compounds, but their herbicidal activity tends to decrease to an unnegligible degree.

The present inventors have found unexpectedly and surprisingly that the 2-methyl or halo-3 and/or 5-methyl-4-halo-substituted phenoxycarboxylic acid anilide compounds of general formula (I) not described in the literature, although varying with the species of weeds, show about 2 to about 5 times as high a herbicidal activity as the 2,4-D or MCP type herbicidal anilide compounds, about $\Delta$ to $\frac{1}{4}$ as low a phytotoxicity to gramineous crops as the aforesaid anilide-type compounds, and about 8 to about 10 times as high a selectivity between weeds and gramineous crops as the aforesaid anilide-type compounds.

The novel compounds of formula (1) also have the advantage that their phytotoxicity to the roots of gramineous plants crops is extremely reduced as compared with MCPCA specifically shown as one herbicidal ingredient of the mixed herbicide disclosed in the above-cited Japanese Patent Publication No. 40731/1973. This is presumably because the reaching of these compounds to a deep site in the soil is low. Another advantage of the novel compounds of formula (I) is that they show a prolonged residual effect in the soil, and exhibit a broadened range of the suitable period of application.

It has also been found that the compounds of formula (1) have higher herbicidal activity and lower phytotoxicity to gramineous crops than $\alpha$-($\beta$-naphthoxy)propionanilide (MT-101) which is said to be the best anilide-type herbicide, as shown in Table 1 given hereinafter.

It has further been found that the herbicidal compounds of formula (1) of this invention can be used in combination with other herbicidally active compounds, and as will be described hereinafter, a combination of small amounts of the herbicidal compound of formula (I) and another herbicidally active compound shows an excellent synergistic effect against both annual and perennial weeds while causing no phytotoxicity to gramineous crops.

It is an object of this invention therefore to provide the compounds of formula (1) not described in the prior art literature, and a process for their production.

Another object of this invention is to provide a tri- or tetra-substituted phenoxycarboxylic acid anilide-type herbicide having unique herbicidal activity and a method for controlling the growth of undesired vegetation.

The above and other objects and advantages of this invention will become more apparent from the following description.

The compounds of this invention are tri- or tetra-substituted phenoxycarboxylic acid anilide-type compounds represented by the following formula

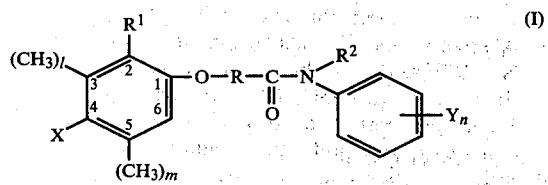

wherein R, $R^1$, $R^2$, X, Y, l, m and n are as defined hereinabove.

In formula (I), R represents a linear or branched lower alkylene or alkenylene group, and specific examples include $C_1$-$C_4$ alkylene or alkenylene groups such as methylene, ethylene, trimethylene, ethylidene and propenylene groups.

In formula (I), $R^1$ represents a methyl group or a halogen atom, and fluorine, chlorine, bromine and iodine atoms can be used as the halogen atom.

$R^2$ in formula (I) represents a hydrogen atom, a lower alkyl group, a lower alkoxy group or a hydroxyl group. Examples of the lower alkyl group are $C_1$-$C_4$ alkyl groups such as methyl, ethyl, n-propyl, i-propyl, n-butyl, i-butyl and tert-butyl groups. Examples of the lower alkoxy group are $C_1$-$C_4$ alkoxy groups such as methoxy, ethoxy, n-propoxy, i-propoxy, n-butoxy, i-butoxy and tert-butoxy groups.

X in formula (I) represents a halogen atom such as fluorine, chlorine, bromine or iodine.

In formula (I), Y represents a member of the class consisting of lower alkyl groups, halogenated lower alkyl groups, lower alkoxy groups, halogen atoms, a nitro group, a cyano group, a hydroxyl group, an amino group, lower alkylamino groups, lower alkanoyloxy groups, lower alkonoylamino groups, lower alkylthio groups, lower alkylsulfonyl groups, lower alkanoyl groups, a carboxyl group, lower alkoxycarbonyl groups and lower alkylaminocarbonyl groups.

The lower alkyl and alkoxy groups for Y may be $C_1$-$C_4$ alkyl and alkoxy groups as exemplified for $R^2$ above.

Examples of the halogen atom Y are the same as those given for $R^1$ above.

The halogenated lower alkyl groups are, for example, $C_1$-$C_4$, preferably $C_1$-$C_2$, alkyl groups having 1 to 3 halogen atoms such as those exemplified with regard to $R^1$. When two or more halogen atoms are present, they may be identical or different. Specific examples of the halogenated $C_1$-$C_4$ alkyl group are trifluoromethyl, 2,2,2-trichloroethyl and 2,2-dibromoethyl groups.

The lower alkylamino groups may be mono- or di-($C_1$-$C_4$ alkyl)-amino groups. In the case of di-(lower alkyl)amino groups, the two alkyl groups may be identical or different. Specific examples of the alkylamino groups include dimethylamino, ethylamino, diethylamino, n-propylamino, i-propylamino, di-n-propylamino, di-i-propylamino, n-butylamino, i-butylamino, di-n-butylamino, N-methylethylamino and N-methyl-n-butylamino groups.

The lower alkanoyloxy groups may be $C_2$-$C_4$ alkanoyloxy groups, and specific examples include ethanoyloxy, propanoyloxy and n-butanoyloxy groups.

The lower alkanoylamino groups may be alkanoylamino groups having 2 to 4 carbon atoms, and specific examples include ethanoylamino, propanoylamino and n-butanoylamino groups.

The lower alkylthio groups may be $C_1$-$C_4$ alkylthio groups, and specific examples include methylthio, ethylthio, n-propylthio, i-propylthio and n-butylthio groups.

The lower alkylsulfonyl groups may be $C_1$-$C_4$ alkylsulfonyl groups, specific examples of which include methylsulfonyl, ethylsulfonyl, n-propylsulfonyl, i-propylsulfonyl and n-butylsulfonyl groups.

The lower alkanoyl groups may be $C_2$-$C_4$ alkanoyl groups, specific examples of which are ethanoyl, propanoyl and n-butanoyl groups.

The lower alkoxycarbonyl groups may be $C_1$-$C_4$ alkoxycarbonyl groups, specific examples of which include methoxycarbonyl, ethoxycarbonyl, n-propoxycarbonyl, i-propoxycarbonyl, and n-butoxycarbonyl groups.

The lower alkylaminocarbonyl groups may be mono- or di-($C_1$–$C_4$ alkyl)-aminocarbonyl groups. In the case of di-lower alkyl-aminocarbonyl groups, the two alkyl groups may be identical or different. Examples of such lower alkylaminocarbonyl groups include methylaminocarbonyl, dimethylaminocarbonyl, ethylaminocarbonyl, diethylaminocarbonyl, i-propylaminocarbonyl and N-methyl-n-butylaminocarbonyl groups.

Specific examples of the novel compounds of formula (1) in accordance with this invention are given below.

TABLE A-1

Compound No.

(1) 2-(2,4-Dichloro-3-methylphenoxy)acetanilide,
(2) 2-(2,4-dichloro-5-methylphenoxy)acetanilide,
(3) 2-(4-chloro-2,3-dimethylphenoxy)acetanilide,
(4) 2-(4-chloro-2,5-dimethylphenoxy)acetanilide,
(5) 2-(2-bromo-4-chloro-3-methylphenoxy)acetanilide,
(6) 2-(4-bromo-2-chloro-5-methylphenoxy)acetanilide,
(7) 2-(2,4-dichloro-3,5-dimethylphenoxy)acetanilide,
(8) 2-(2,4-dichloro-3-methylphenoxy)propionanilide,
(9) 2-(2,4-dichloro-5-methylphenoxy)propionanilide,
(10) 2-(4-chloro-2,3-dimethylphenoxy)propionanilide,
(11) 2-(4-chloro-2,5-dimethylphenoxy)propionanilide,
(12) 2-(2-bromo-4-chloro-3-methylphenoxy)propionanilide,
(13) 2-(4-bromo-2-chloro-5-methylphenoxy)propionanilide,
(14) 2-(2,4-dichloro-3,5-dimethylphenoxy)propionanilide,
(15) 4-(2,4-dichloro-3-methylphenoxy)butyranilide,
(16) 4-(2,4-dichloro-5-methylphenoxy)butyranilide,
(17) 4-(4-chloro-2,3-dimethylphenoxy)butyranilide,
(18) 4-(4-chloro-2,5-dimethylphenoxy)butyranilide,
(19) 4-(2-bromo-4-chloro-3-methylphenoxy)butyranilide,
(20) 4-(4-bromo-2-chloro-5-methylphenoxy)butyranilide,
(21) 4-(2,4-dichloro-3,5-dimethylphenoxy)butyranilide,
(22) 4-(2,4-dichloro-3-methylphenoxy)valeranilide,
(23) 4-(2,4-dichloro-5-methylphenoxy)valeranilide,
(24) 4-(4-chloro-2,3-dimethylphenoxy)valeranilide,
(25) 4-(4-chloro-2,5-dimethylphenoxy)valeranilide,
(26) 4-(2-bromo-4-chloro-3-methylphenoxy)valeranilide,
(27) 4-(4-bromo-2-chloro-5-methylphenoxy)valeranilide,
(28) 4-(2,4-dichloro-3,5-dimethylphenoxy)valeranilide,
(29) 4-(2,4-dichloro-3-methylphenoxy)crotonanilide,
(30) 4-(2,4-dichloro-5-methylphenoxy)crotonanilide,
(31) 4-(4-chloro-2,3-dimethylphenoxy)crotonanilide,
(32) 4-(4-chloro-2,5-dimethylphenoxy)crotonanilide,
(33) 4-(2-bromo-4-chloro-3-methylphenoxy)crotonanilide,
(34) 4-(4-bromo-2-chloro-5-methylphenoxy)crotonanilide,
(35) 4-(2,4-dichloro-3,5-dimethylphenoxy)crotonanilide,
(36) 4-(2,4-dichloro-3-methylphenoxy)-2-pentenoanilide,
(37) 4-(2,4-dichloro-5-methylphenoxy)-2-pentenoanilide,
(38) 4-(4-chloro-2,3-dimethylphenoxy)-2-pentenoanilide,
(39) 4-(4-chloro-2,5-dimethylphenoxy)-2-pentenoanilide,
(40) 4-(2-bromo-4-chloro-3-methylphenoxy)-2-pentenoanilide,
(41) 4-(4-bromo-2-chloro-5-methylphenoxy)-2-pentenoanilide,
(42) 4-(2,4-dichloro-3,5-dimethylphenoxy)-2-pentenoanilide,
(43) 2-(2,4-dichloro-3-methylphenoxy)butyranilide,
(44) 2-(2,4-dichloro-5-methylphenoxy)butyranilide,
(45) 2-(2,4-dichloro-3,5-dimethylphenoxy)butyranilide,
(46) 2-(2,4-dichloro-3-methylphenoxy)isovaleranilide,
(47) 2-(2,4-dichloro-5-methylphenoxy)isovaleranilide,
(48) 2-(2,4-dichloro-3,5-dimethylphenoxy)isovaleranilide,
(49) 2-(2,4-dichloro-5-methylphenoxy)-N-methylacetanilide,
(50) 2-(2,4-dichloro-3-methylphenoxy)-N-methylpropionanilide,
(51) 2-(2,4-dichloro-3,5-dimethylphenoxy)-N-methylpropionanilide,
(52) 4-(2,4-dichloro-3-methylphenoxy)-N-methylbutyranilide,
(53) 4-(2,4-dichloro-3-methylphenoxy)-N-methylvaleranilide,
(54) 2-(2,4-dichloro-3-methylphenoxy)-N-methoxypropionanilide,
(55) 2-(2,4-dichloro-3-methylphenoxy)-N-hydroxypropionanilide,
(56) 2-(2,4-dichloro-3-methylphenoxy)-4'-methylpropionanilide,
(57) 2-(2,4-dichloro-3-methylphenoxy)-2'-methylpropionanilide,
(58) 2-(2,4-dichloro-3-methylphenoxy)-3'-methylpropionanilide,
(59) 2-(2,4-dichloro-3-methylphenoxy)-3'-trichloromethylpropionanilide,
(60) 2'-chloro-2-(2,4-dichloro-5-methylphenoxy)acetanilide,
(61) 2'-chloro-2-(2,4-dichloro-3-methylphenoxy)propionanilide,
(62) 4'-chloro-2-(2,4-dichloro-3-methylphenoxy)propionanilide,
(63) 3'-chloro-2-(2,4-dichloro-5-methylphenoxy)propionanilide,
(64) 2-(2,4-dichloro-3-methylphenoxy)-2'-methoxypropionanilide,
(65) 2-(2,4-dichloro-3-methylphenoxy)-3'-methoxypropionanilide,
(66) 2-(2,4-dichloro-3-methylphenoxy)-4'-methoxypropionanilide,
(67) 2-(2,4-dichloro-3-methylphenoxy)-2'-nitroacetanilide,
(68) 2-(2,4-dichloro-3-methylphenoxy)-4'-nitropropionanilide,
(69) 2-(2,4-dichloro-5-methylphenoxy)-2'-nitropropionanilide,
(70) 2'-cyano-2-(2,4-dichloro-3-methylphenoxy)propionanilide,
(71) 3'-cyano-2-(2,4-dichloro-5-methylphenoxy)acetanilide,
(72) 4'-cyano-2-(2,4-dichloro-5-methylphenoxy)propionanilide,
(73) 2-(2,4-dichloro-3-methylphenoxy)-2'-hydroxypropionanilide,

(74) 2-(2,4-dichloro-3-methylphenoxy)-3'-hydroxypropionanilide,
(75) 2-(2,4-dichloro-3-methylphenoxy)-4'-hydroxypropionanilide,
(76) 2-(2,4-dichloro-5-methylphenoxy)-2'-hydroxyacetanilide,
(77) 2'-amino-2-(2,4-dichloro-3-methylphenoxy)propionanilide,
(78) 3'-amino-2-(2,4-dichloro-3-methylphenoxy)propionanilide,
(79) 4'-amino-2-(2,4-dichloro-3-methylphenoxy)propionanilide,
(80) 2'-(2,4-dichloro-3-methylphenoxy)-2'-dimethylaminopropionanilide,
(81) 2-(2,4-dichloro-3-methylphenoxy)-3'-methylaminopropionanilide,
(82) 2-(2,4-dichloro-5-methylphenoxy)-4'-diethylaminopropionanilide,
(83) 2'-acetoxy-2-(2,4-dichloro-3-methylphenoxy)propionanilide,
(84) 3'-acetoxy-2-(2,4-dichloro-3-methylphenoxy)propionanilide,
(85) 4'-acetoxy-2-(2,4-dichloro-3-methylphenoxy)propionanilide,
(86) 2-(2,4-dichloro-3-methylphenoxy)-3'-methylaminocarbonyloxypropionanilide,
(87) 2-(2,4-dichloro-3-methylphenoxy)-3'-dimethylaminocarbonyloxypropionanilide,
(88) 2'-acetamino-2-(2,4-dichloro-3-methylphenoxy)propionanilide,
(89) 4'-acetamino-2-(2,4-dichloro-3-methylphenoxy)propionanilide,
(90) 2-(2,4-dichloro-3-methylphenoxy)-4'-methylsulfonylpropionanilide,
(91) 2-(2,4-dichloro-5-methylphenoxy)-4'-methylsulfonylpropionanilide,
(92) 2'-acetyl-2-(2,4-dichloro-3-methylphenoxy)propionanilide,
(93) 4'-acetyl-2-(2,4-dichloro-5-methylphenoxy)propionanilide,
(94) 2'-carboxy-2-(2,4-dichloro-3-methylphenoxy)propionanilide,
(95) 3'-carboxy-2-(2,4-dichloro-5-methylphenoxy)propionanilide,
96) 4'-carboxy-2-(2,4-dichloro-5-methylphenoxy)propionanilide,
(97) 2-(2,4-dichloro-3-methylphenoxy)-2'-methoxycarbonylpropionanilide,
(98) 2-(2,4-dichloro-5-methylphenoxy)-3'-methoxycarbonylpropionanilide,
(99) 2-(2,4-dichloro-3-methylphenoxy)-4'-methoxycarbonylpropionanilide,
(100) 2-(2,4-dichloro-3-methylphenoxy)-2'-diethylaminocarbonylpropionanilide,
(101) 2-(2,4-dichloro-3-methylphenoxy)-3'-methoxycarbonylaminopropionanilide,
(102) 2-(2,4-dichloro-3-methylphenoxy)isovaleranilide,
(103) 2-(2,4-dichloro-5-methylphenoxy)isovaleranilide,
(104) 2-(2,4-dichloro-3-methylphenoxy)-2',6'diethylpropionanilide,
(105) 2-(2,4-dichloro-5-methylphenoxy)-2',6'-diethylpropionanilide,
(106) 3',4'-dichloro-2-(2,4-dichloro-3-methylphenoxy)propionanilide,
(107) 2',5'-dichloro-2-(2,4-dichloro-3-methylphenoxy)propionanilide,
(108) 2-(2,4-dichloro-3-methylphenoxy)-2'-fluoropropionanilide,
(109) 2-(2,4-dichloro-3-methylphenoxy)-3'-fluoropropionanilide,
(110) 2-(2,4-dichloro-3-methylphenoxy)-4'-fluoropropionanilide, and
(111) 2-(2,4-dichloro-3-methylphenoxy)-4'-methylthiopropionanilide.

The compounds of formula (1) of this invention can be produced by reacting a phenoxycarboxylic acid halide derivative of formula (XI) with an aniline derivative of formula (XII) preferably in the presence of an acid binder by a technique similar to those disclosed in the above-cited Japanese Laid-Open Patent Publication No. 96323/1978 and British Pat. No. 1,041,982 except that the substituents on the benzene ring of the phenoxy moiety of formula (I) are the same types of substituents as specified in formula (I) and substituted at the positions specified in formula (I).

Accordingly, the present invention provides a process for producing the compounds of formula (I) which comprises reacting a phenoxycarboxylic acid halide compound of the formula

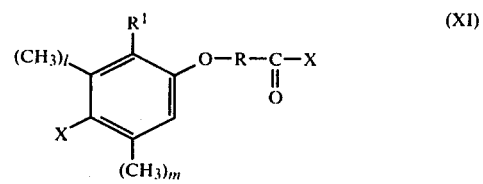

wherein R, $R^1$, X, l and m are as defined with regard to formula (I), and two X's may be identical or different,
with an aniline derivative of the formula

wherein $R^2$, Y and n are as defined with regard to formula (I).

An example of this process is schematically shown below.

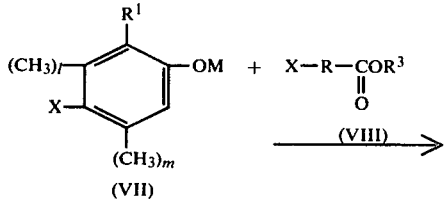

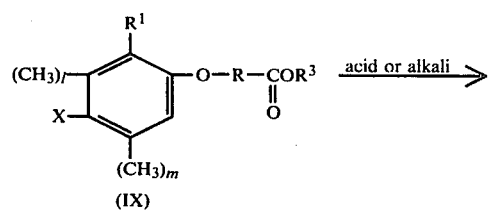

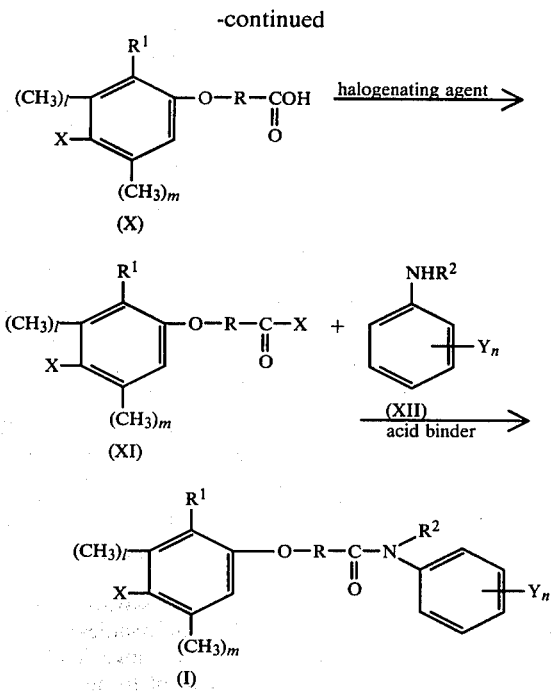

In the above scheme, R, $R^1$, $R^2$, X, Y, l, m and n are as defined with regard to formula (I); M represents an alkali metal atom such as sodium or potassium; and $R^3$ represents a lower alkyl group preferably having 1 to 4 carbon atoms.

In the above process, the phenoxycarboxylic acid ester derivative (IX) can be easily produced by reacting the alkali metal salt of formula (VII) of a substituted phenol with the halogenated alkyl carboxylate of formula (VIII). This reaction is suitably carried out in the presence of a solvent. Examples of useful solvents include alcohols such as methanol, ethanol and isopropanol, ethers such as tetrahydrofuran and dioxane, ketones such as acetone and methyl ethyl ketone, acetonitrile, dimethyl sulfoxide, dimethyl formamide, and mixtures of these. The alcohols and ethers are preferred. There is no particular limitation on the reaction temperature. For example, the reaction can be carried out at a temperature ranging from room temperature to the refluxing temperature of the solvent. Preferably, it is carried out at the refluxing temperature of the solvent or a temperature close to it. The reaction time varies depending upon the type of the reagents used, the reaction temperature, etc. For example, it is about 1 hour to about 20 hours. If desired, the resulting ester (IX) may be isolated in a customary manner. It is not particularly necessary, however, to separate and purify it, and the crude product suffices for use in the subsequent hydrolyzing step.

Hydrolysis of the compound (IX) to the phenoxycarboxylic acid derivative of formula (X) readily takes place in the presence of an acid or alkali. Examples of the acid used are mineral acids such as hydrochloric acid and sulfuric acid, and examples of the alkali include alkali metal hydroxides such as sodium hydroxide and potassium hydroxide. Mineral acids such as hydrochloric acid and sulfuric acid are especially preferred. Preferably, the hydrolysis is carried out in the presence of a solvent, for example alcohols such as methanol, ethanol and isopropanol, and lower fatty acids such as acetic acid and propionic acid. There is no particular restriction on the reaction temperature, and for example, temperatures ranging from room temperature to the refluxing temperature of the solvent can be employed. Preferably, the refluxing temperature of the solvent or temperatures close to it are used. The reaction temperature is, for example, about 1 to about 10 hours, although varying depending upon the type of the acid or alkali used, the reaction temperature, etc.

Alternatively, the phenoxycarboxylic acid derivative (X) may also be obtained directly by reacting the alkali metal salt (VII) of a substituted phenol with a halocarboxylic acid in the presence of an alkali metal hydroxide such as sodium hydroxide and potassium hydroxide.

The phenoxycarboxylic acid derivative (X) so obtained in treated with a halogenating agent such as thionyl chloride, phosphorus pentachloride and phosphorus tribromide to give the phenoxycarboxylic acid halide (XI) easily.

By reacting the resulting acid halide derivative (XI) with the aniline derivative (XII) preferably in the presence of an acid binder, the phenoxycarboxylic acid anilide derivative (I), the herbicidal compounds of this invention, can be easily produced. Examples of the acid binder used in this reaction include inorganic bases such as sodium hydroxide, potassium hydroxide, sodium carbonate, potassium carbonate and sodium bicarbonate; and organic bases such as pyridine and triethylamine. Preferably, the reaction is carried out in a solvent which is inert to the reaction. Examples of the solvent are ethers such as diethyl ether, tetrahydrofuran and dioxane, aromatic hydrocarbons such as benzene, toluene and xylene, halogenated hydrocarbons such as dichloromethane, chloroform and carbon tetrachloride, ketones such as acetone and methyl ethyl ketone, esters such as ethyl acetate, acetonitrile, dimethyl sulfoxide, dimethyl formamide, and mixtures of these.

There is no particular restriction on the reaction temperature, and for example, temperatures ranging from room temperature to the refluxing temperature of the solvent may be exemplified. The reaction time varies depending upon the reaction temperature, the type of the reagents used, etc., and is, for example, about 1 to several hours. After the reaction, the desired compound of formula (I) can be isolated from the reaction mixture in a customary manner.

The phenoxycarboxylic acid anilide derivative (I) may also be obtained by reacting the phenoxycarboxylic acid derivative (X) with the aniline derivative (XII) in the presence of a dehydrating agent such as phosphorus pentoxide, phosphorus oxychloride, DCC, etc.

According to this invention, there can be provided a herbicidal composition comprising an effective amount of the compound of formula (I) and a liquid or solid diluent or carrier.

The present invention also provides a method for controlling the growth of undesired vegetation which comprises applying an effective amount of the compound of formula (I) to the locus to be protected from weeds.

The compounds (I) of this invention exhibit the aforesaid excellent and unique herbicidal activity, and can selectively control a broad range of paddy weeds, for example weeds of the family Cyperaceae such as umbrella plant (*Cyperus difformis*) and *Cyperus serotinus*, broadleaved weeds such as *Monochoria vaginalis, Rotala indica, Lindernia pyxidaria, Dopatrium junceum, Labelia radicans* and *Elipta alba*, and perennial weeds such as

*Eleocharis acicularis, Scirpus hotarui, Sagittaria pygmaea, Alisma canaliculatum,* and *Oenanthe javanica* without causing phytotoxicity to gramineous crops.

The herbicidal compound of formula (I) of this invention can be used either as such or as a composition comprising a combination of it with a suitable liquid or solid carrier or diluent and optionally other additives or adjuvants. The composition may be used in various forms prepared by known techniques for agricultural chemical production, such as wettable powders, solutions, dusts, emulsifiable concentrates and granules. Such solid or liquid carriers or diluents and other additives and adjuvants are well known in the art, and can be suitably selected for use in the present invention.

Examples of solid carriers or diluents include clays typified by clays of the kaolinite, montmorillonite and attapulgite groups; inorganic substances such as talc, mica, pyrophyllite, pumice, vermiculite, gypsum, calcium carbonate, diatomaceous earth, magnesium lime, phosphorus lime, zeolite and silicic anhydride; vegetable organic substances such as soybean meal, wheat flour and crystalline cellulose; synthetic or natural polymeric compounds such as petroleum resins, polyvinyl chloride, polyalkylene glycols, ketone resins, ester gum and copal gum; and urea.

Examples of the liquid carriers or diluents are any liquids which are solvents, or non-solvents capable of dispersing or dissolving the compounds of this invention by the aid of adjuvants. Specific examples include paraffinic or naphthenic hydrocarbons such as kerosene, mineral oils, spindle oils, and white oils; aromatic hydrocarbons such as benzene, toluene, xylene, ethylbenzene, cumene and methylnaphthalene; chlorinated hydrocarbons such as carbon tetrachloride, chloroform, trichloroethylene, monochlorobenzene and o-chlorobenzene; ethers such as dioxane and tetrahydrofuran; ketones such as acetone, methyl ethyl ketone, isobutyl ketone, cyclohexanone and isophorone; esters such as ethyl acetate, amyl acetate, ethylene glycol acetate, diethylene glycol acetate and diethyl succinate; alcohols such as methanol, n-hexanol, ethylene glycol and diethylene glycol; ether alcohols such as ethylene glycol ethyl ether, diethylene glycol ethyl ether and diethylene glycol butyl ether; dimethyl formamide; and dimethyl sulfoxide.

In order to improve the emulsifiability, dispersibility, spreadability, etc. of the compounds of this invention, surface-active agents and other adjuvants may be used. The surface-active agents may be nonionic, anionic and cationic surface-active agents. Examples of suitable nonionic surface-active agents are polyaddition products of ethylene with higher alcohols such as lauryl alcohol, stearyl alcohol and oleyl alcohol, polyaddition products of ethylene oxide with alkylphenols or alkylnaphthols such as isooctylphenol, nonylphenol, octylnaphthol and butylnaphthol, polyaddition products of ethylene oxide with higher fatty acids such as palmitic acid, stearic acid, and oleic acid, polyaddition products of ethylene oxide with amino compounds such as dodecylamine and stearamide, and polyaddition products of ethylene oxide with mono- or dialkylphosphoric acids such as stearylphosphoric acid and dilaurylphosphoric acid. Examples of the anionic surface-active agents include alkylsulfate ester salts such as sodium laurysulfonate and an amine salt of oleys alcohol/sulfuric acid ester, alkylsulfonic acid salts such as dioctyl sulfosuccinate sodium salt and sodium 2-ethylhexyl-2-ethylhexenesulfonate, and arylsulfonic acid salts such as sodium isopropylnapthalenesulfonate, sodium lignosulfonate and sodium dodecylbenzenesulfonate.

The above-exemplfied carriers or diluents and additives or adjuvants may be used singly or in combination according to the purpose of using the final composition in consideration of the form of the composition, the site of application, etc.

The amount of the compound of formula (I) in the composition of this invention can be properly selected within a wide range, and for example, is about 0.1 to about 99.0% by weight based on the weight of the composition.

The tri- or tetra-substituted phenoxycarboxylic acid anilide herbicide of this invention represented by formula (I) can be applied as such (I) or in other desired forms. It may be applied to upland farms, but application to rice paddies is especially suitable. The rate of application, or the dosage, can be suitably varied depending upon the type of weeds to be controlled, the time and place of application, the weather, etc. For example, the amount of the compound (I) to be applied is about 1 to about 1000 g, preferably about 5 to about 500 g, per 10 ares. In particular, perennial weeds which have frequently occurred in aquatic paddies in recent years causing great hazards can be conveniently controlled by applying the compound of formula (I) at a rate of about 20 to about 400 g, preferably about 50 to about 200 g, per 10 ares.

The tri- or tetra-substituted phenoxycarboxylic acid anilide herbicide of this invention can be applied together with another herbicide or in the form of a composition comprising a combination of it with the other herbicide, and this can frequently bring about a synergistic effect. Furthermore, in order to decrease the number of applications, the compound of this invention may be used as a mixture with another agricultural chemical such as an insecticide or a plant growth regulator, or together with such other agricultural chemical. It can also be used in combination with a fertilizer, a soil conditioner, etc.

By one application of the herbicidal compound of formula (I) of this invention and the other herbicidal compound in reduced amounts, both annual and perennial weeds can be controlled with excellent herbicidal activity without causing phytotoxicity to gramineous plants. Preferably, the other herbicidal compounds may be those which are selected from so-called "barnyard grass herbicides" and exhibit a marked synergistic effect. Examples of such other herbicidal compounds are compounds (1) to (9) given below.

(1) α-Chloro-2',6'-diethyl-N-(butoxymethyl)-acetanilide (Butachlor), (2) α-chloro-2',6'-diethyl-N-(propoxyethyl)-acetanilide (CG-113), (3) S-ethyl-N,N-hexamethylenethiolcarbamate (Molinate), (4) S-(4-clorobenzyl)-N,N-diethylthiolcarbamate (Benthiocarb), (5) S-(αα-dimethylbenzyl)-N,N-pentamethylene-thiocarbamate (MY-93), (6) O,O-diisopropyl-S-(2-benzenesulfonylaminoethyl)-phosphorodithioate (SAP), (7) O-ethyl-O-(2-nitro-5-methylphenyl)-N-sec.-butyl-phosphoramidothioate (Cremart), (8) O,O-diisopropyl-S-(2-methylpiperidin-1-yl-carbonylmethyl)phosphorodoithioate (Piperophos), (9) O,O-diphenyl-S-(2-methylpiperidin-1-yl-carbonylmethyl)-phosphorodithioate (DP-Piperophos).

Thus, according to one embodiment of the invention, there is provided a mixed herbicide comprising (A) the trior tetra substituted phenoxycarboxylic acid anilide-type compound (I) and (B) at least one member selected from the compounds (1) to (9) above as active ingredients. Mixed herbicides comprising the compound of formula (I) and the compound (1) or (2) exhibit especially outstanding synergistic effects.

The ratio of component (A) to component (B) in this embodiment can be suitably selected. When the acetanilide compound (1) or (2) is selected as the component (B), the weight ratio of (A) to (B) is preferably 1:about 0.05-about 2, more preferably 1:about 0.2 to about 1.5. When the thiol carbamates (3) to (5) are selected as the component (B), the weight ratio of component (A) to component (B) is 1:about 0.25-about 8, more preferably 1:about 0.5-about 4. When the phosphorodithioates (6) to (9) are selected as the component (B), the weight ratio of (A) to (B) is preferably 1:about 0.1-about 5, more preferably 1:about 0.25-about 2. The rate of application of the mixed herbicide in this embodiment can also be selected properly. For example, the total amount of the components (A) and (B) to be applied is about 10 to about 1000 g, preferably about 25 to about 600 g, per 10 ares. In this embodiment, too, the active compounds may be directly applied, or in the various forms prepared as described hereinabove.

The following examples illustrate the production of the herbicidal compound of formula (I), the preparation of the herbicidal composition and the testing of the herbicidal effect of the compound (I) or the composition thereof.

PRODUCTION EXAMPLE 1

2-(2,4-Dichloro-3-methylphenoxy)propionic acid:

In 100 ml of ethanol was dissolved 10.0 g. (0.05 mole) of sodium 2,4-dichloro-3-methylphenolate. With stirring at room temperature, 9.1 g (0.05 mole) of ethyl 2-bromopropionate was added. The mixture was heated under reflux for 4 hours. The ethanol was distilled off under reduced pressure, and the residue was extracted with 50 ml of diethyl ether. The ethereal layer was washed with 25 ml of a 5% aqueous solution of sodium hydroxide and 25 ml of water, and dried over anhydrous magnesium sulfate. The dessicant was removed by filtration, and the diethyl ether was distilled off to give 11.8 g of crude ethyl 2-(2,4-dichloro-3-methylphenoxy)propionate. The crude ester (11.8 g) was dissolved in 100 ml of glacial acetic acid. Concentrated hydrochloric acid (25 ml) was added, and the mixture was stirred at 100° C. for 40 minutes. The reaction mixture was cooled, and poured onto 300 ml of ice water. The precipitated crystals were filtered, washed with water, and dried to give 9.2 g of 2-(2,4-dichloro-3-methylphenoxy)-propionic acid. The yield was 73.9% based on the sodium 2,4-dichloro-3-methylphenolate, and the final product had a melting point of 149.5 to 150.5° C.

PRODUCTION EXAMPLE 2

2-(2,4-Dichloro-3-methylphenoxy)propionanilide:

Thionyl chloride (17.9 g; 0.15 mole) was added to 12.5 g (0.05 mole) of 2-(2,4-dichloro-3-methylphenoxy)-propionic acid, and the mixture was heated under reflux for 3 hours. The excess of thionyl chloride was distilled off from the reaction mixture to give 14.2 g of crude 2-(2,4-dichloro-3-methylphenoxy)propionyl chloride. A solution of 14.2 g of the crude chloride in 50 ml of diethyl ether was added dropwise to a mixture of 4.65 g (0.05 mole) and 40 g (0.05 mole) of a 5% aqueous solution of sodium hydroxide with stirring over the course of 15 minutes. The mixture was then stirred at room temperature for 1 hour. The precipitated solid was collected by filtration, washed with water and dried. Recrystallization from hexane yielded 10.7 g of the desired product as colorless needles. Yield: 66.0%; melting point 147.5 to 148.0° C.

PRODUCTION EXAMPLE 3

By the same procedure as in Production Examples 1 and 2, the compounds of formula (I) shown in Table A-2 were obtained.

TABLE A-2

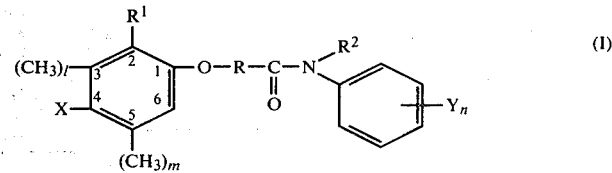

(I)

| Compound No. | R¹ | l(CH₃) | X | m(CH₃) | R | R² | Yₙ | Melting point (°C.) |
|---|---|---|---|---|---|---|---|---|
| 1 | Cl | 1 | Cl | 0 | CH₂ | H | — | 114.5–116.5 |
| 8 | Cl | 1 | Cl | 0 | CH(CH₃) | H | — | 147.5–148 |
| 9 | Cl | 0 | Cl | 1 | CH(CH₃) | H | — | 125.5–127 |
| 10 | CH₃ | 1 | Cl | 0 | CH(CH₃) | H | — | 84–86 |
| 12 | Br | 1 | Cl | 0 | CH(CH₃) | H | — | 150–150.5 |
| 14 | Cl | 1 | Cl | 1 | CH(CH₃) | H | — | 127.5–128 |
| 15 | Cl | 1 | Cl | 0 | (CH₂)₃ | H | — | 133.5–134.5 |
| 29 | Cl | 1 | Cl | 0 | —CH₂CH=CH— | H | — | 141–142 |
| 36 | Cl | 1 | Cl | 0 | CH₃<br>\|<br>—CHCH=CH— | H | — | 132.5–134 |

| Compound No. | R¹ | l | X | m | R | R² | Yₙ | Melting point (°C.) |
|---|---|---|---|---|---|---|---|---|
| 50 | Cl | 1 | Cl | 0 | CH(CH₃) | CH₃ | — | 100.5–102 |
| 55 | Cl | 1 | Cl | 0 | CH(CH₃) | OH | — | 185–190 (decomp.) |
| 56 | Cl | 1 | Cl | 0 | CH(CH₃) | H | 4'-CH₃ | 132.5–133.5 |
| 57 | Cl | 1 | Cl | 0 | CH(CH₃) | H | 2'-CH₃ | 151–151.5 |

TABLE A-2-continued $$(CH_3)_l \underset{X}{\overset{R^1}{\underset{\underset{(CH_3)_m}{|}}{\bigodot}}} O-R-\underset{\underset{O}{\|}}{C}-N\underset{R^2}{\overset{}{\bigodot}}Y_n \quad (I)$$

| No. | X | l | R¹ | m | R | R² | Y | mp (°C) |
|---|---|---|---|---|---|---|---|---|
| 58 | Cl | 1 | Cl | 0 | CH(CH₃) | H | 3'-CH₃ | 132-133.5 |
| 59 | Cl | 1 | Cl | 0 | CH(CH₃) | H | 3'-CF₃ | 125-126 |
| 61 | Cl | 1 | Cl | 0 | CH(CH₃) | H | 2'-Cl | 104.5-105 |
| 62 | Cl | 1 | Cl | 0 | CH(CH₃) | H | 4'-Cl | 152-152.5 |
| 64 | Cl | 1 | Cl | 0 | CH(CH₃) | H | 2'-OCH₃ | 102.5-105.0 |
| 66 | Cl | 1 | Cl | 0 | CH(CH₃) | H | 4'-OCH₃ | 170.5-171.5 |
| 68 | Cl | 1 | Cl | 0 | CH(CH₃) | H | 4'-NO₂ | 200-201.5 |
| 70 | Cl | 1 | Cl | 0 | CH(CH₃) | H | 2'-CN | 147.5-149 |
| 74 | Cl | 1 | Cl | 0 | CH(CH₃) | H | 3'-OH | 185-186.5 |
| 75 | Cl | 1 | Cl | 0 | CH(CH₃) | H | 4'-OH | 161-162 |
| 79 | Cl | 1 | Cl | 0 | CH(CH₃) | H | 4'-NH₂ | 169.5-170.5 |
| 85 | Cl | 1 | Cl | 0 | CH(CH₃) | H | 4'-OCCH₃ (O=) | 165-166 |
| 89 | Cl | 1 | Cl | 0 | CH(CH₃) | H | 4'-NHCCH₃ (O=) | 225-226 |
| 90 | Cl | 1 | Cl | 0 | CH(CH₃) | H | 4'-SO₂CH₃ | 152-152.5 |
| 92 | Cl | 1 | Cl | 0 | CH(CH₃) | H | 2'-CCH₃ (O=) | 114-116 |
| 94 | Cl | 1 | Cl | 0 | CH(CH₃) | H | 2'-CO₂H | 188-189.5 |
| 97 | Cl | 1 | Cl | 0 | CH(CH₃) | H | 2'-CO₂CH₃ | 78-79.5 |
| 104 | Cl | 1 | Cl | 0 | CH(CH₃) | H | 2',-diC₂H₅ | 180-180.5 |
| 106 | Cl | 1 | Cl | 0 | CH(CH₃) | H | 3',4'-diCl | 164.5-165 |
| 107 | Cl | 1 | Cl | 0 | CH(CH₃) | H | 2',5'-diCl | 114.0-116.0 |
| 108 | Cl | 1 | Cl | 0 | CH(CH₃) | H | 2'-F | 110-111 |
| 109 | Cl | 1 | Cl | 0 | CH(CH₃) | H | 3'-F | 135.5-136.5 |
| 110 | Cl | 1 | Cl | 0 | CH(CH₃) | H | 4'-F | 148.5-150 |
| 111 | Cl | 1 | Cl | 0 | CH(CH₃) | H | 4'-SCH₃ | 172.5-173.5 |

FORMATION EXAMPLE 1

(Emulsifiable Concentrate)

| | |
|---|---|
| Compound No. 8 of the invention | 20 parts |
| Xylene | 70 parts |
| Nonionic surfactant ("Sorpol 800", a registered trademark for a product of Toho Chemical Co., Ltd.) | 10 parts |

The above ingredients were mixed to form an emulsifiable concentrate.

FORMATION EXAMPLE 2

(Wettable Powder)

| | |
|---|---|
| Compound No. 8 of the invention | 50 parts |
| Bentonite | 30 parts |
| Talc | 15 parts |
| Sodium dodecylbenzenesulfonate | 5 parts |

The above ingredients were mixed and pulverized to form a wettable powder.

FORMULATION EXAMPLE 3

(Granules)

| | |
|---|---|
| Compound No. 56 of the invention | 5 parts |
| Mixture of equal amounts of bentonite and talc | 80 parts |
| White carbon | 10 parts |
| Sodium isopropylnaphthalene-sulfonate | 2 parts |
| Sodium lignosulfonate | 3 parts |

The above ingredients were mixed and pulverized and granulated by a granulator in a usual manner, followed by drying, to obtain granules.

FORMULATION EXAMPLE 4

(Granules)

| | |
|---|---|
| Compound No. 8 of the invention | 3 parts |
| Zieklite | 40 parts |
| Clay | 40 parts |
| White carbon | 12 parts |
| Sodium isopropylnaphthalene-sulfonate | 2 parts |
| Sodium lignosulfonate | 3 parts |

The above ingredients were mixed and pulverized and subjected to the same procedure as in Formulation Example 3 to form granules.

FORMULATION EXAMPLE 5

(Granules)

| | | |
|---|---|---|
| Compound No. 8 of the invention | 4 | parts |
| Butachlor | 3 | parts |
| Bentonite | 40 | parts |
| Talc | 48 | parts |
| Sodium dodecylbenzene-sulfonate | 1 | part |
| Polyoxyethylenealkylaryl ether | 1 | part |
| Sodium lignosulfonate | 3 | parts |

The above ingredients were mixed and pulverized, and processed in the same way as in Formulation Example 3 to give granules.

TEST EXAMPLE 1

Test for treating the flooded soil:

Paddy soil was filled in pots having an inside diameter of 12 cm (area 113 $cm^2$) and mixed with water to provide a simulated paddy. Predetermined amounts of the seeds of barnyard grass *Echinochloa crus-galli*, *Cyperus difformis*, *Scirpus hotarui*, *Monochoria vaginalis*, *Alisma canaliculatum* and *Rotala indica* were sown in each pot, and buried to a depth within 1 cm from the soil surface. Two tubers of *Sagittaria pygmaea* were transplanted in each pot, and a set of two closely aligned rice plants in the two-leaf stage was also transplanted in each pot. The soil was then flooded to a water depth of 2 cm. On the third day after the sowing, a dilution of a wettable powder (prepared as shown in Formulation Example 2) of each of the compounds of this invention and comparative compounds shown in Table 1 was applied in a predetermined amount in each pot by means of a pipette. After the treatment of the flooded soil in this way, the pots were allowed to stand in a glass greenhouse, and the plants were grown for 30 days under proper control. The amount of the remaining weeds and the inhibition of the growth of rice in each pot were compared with those in a non-treated pot, and the herbicidal effect and phytotoxicity were evaluated in accordance with the following standards. The results are shown in Table 1.

| Standards of evaluation of the herbicidal effect | |
|---|---|
| Scale | Ratio of the remaining weeds based on the non-treated pot (%) |
| 5 | 0 |
| 4 | 1–10 |
| 3 | 11–20 |
| 2 | 21–40 |
| 1 | 41–60 |
| 0 | 61 or more |
| Standards of evaluation of phytotoxicity | |
| Scale | Percent inhibition of growth based on the non-treated pot (%) |
| — | 0 |
| ± | 1–5 |
| + | 6–15 |
| ++ | 16–25 |
| +++ | 26–50 |
| ++++ | 51 or more |

The letters A to I in the column of "Herbicidal effect" in the following Tables stand for the following weeds.

A: *Echinochloa crus-galli*
B: *Monochoria vaginalis*
C: *Rotala indica*
D: *Cyperus difformis*
E: *Scirpus hotarui*
F: *Alisma canaliculatum*
G: *Sagittaria pygmaea*
H: *Eleocharis acicularis*
I: *Cyperus serotinus*

The numbers of the test compounds in the following tables correspond to those of the compound of the invention represented by general formula (I) and exemplified hereinabove.

MT-101 given in Table 1 and elsewhere represents α-(β-naphthoxy)propioanilide.

TABLE 1

| Test compound | Rate of application (g/10a) | Herbicidal effect | | | | | | | Phytotoxicity to rice |
|---|---|---|---|---|---|---|---|---|---|
| | | A | B | C | D | E | F | G | |
| 1 | 400 | 1.5 | 5 | 5 | 5 | 5 | 5 | 5 | — |
| | 200 | 1 | 5 | 5 | 5 | 5 | 5 | 5 | — |
| | 100 | 0 | 5 | 5 | 5 | 4 | 5 | 4 | — |
| 8 | 100 | 2 | 5 | 5 | 5 | 5 | 5 | 5 | — |
| | 50 | 1.5 | 5 | 5 | 5 | 5 | 5 | 5 | — |
| | 25 | 1.5 | 5 | 5 | 5 | 5 | 5 | 5 | — |
| 9 | 100 | 0 | 5 | 5 | 5 | 5 | 5 | 5 | — |
| | 50 | 0 | 5 | 5 | 5 | 5 | 5 | 5 | — |
| | 25 | 0 | 4 | 4 | 4 | 5 | 4 | 5 | — |
| 12 | 100 | 2 | 5 | 5 | 5 | 5 | 5 | 5 | — |
| | 50 | 1.5 | 5 | 5 | 5 | 5 | 5 | 5 | — |
| | 25 | 1.5 | 5 | 5 | 5 | 5 | 5 | 5 | — |
| 14 | 100 | 2 | 5 | 5 | 5 | 5 | 5 | 5 | — |
| | 50 | 1.5 | 5 | 5 | 5 | 5 | 5 | 5 | — |
| | 25 | 1 | 5 | 5 | 5 | 5 | 5 | 5 | — |
| 50 | 100 | 1.5 | 5 | 5 | 5 | 5 | 5 | 5 | — |
| | 50 | 1 | 5 | 5 | 5 | 5 | 5 | 5 | — |
| | 25 | 1 | 5 | 5 | 5 | 5 | 5 | 5 | — |
| 56 | 400 | 2 | 5 | 5 | 5 | 5 | 5 | 5 | — |
| | 200 | 1.5 | 5 | 5 | 5 | 5 | 5 | 5 | — |
| | 100 | 1 | 5 | 5 | 5 | 5 | 5 | 5 | — |
| 61 | 200 | 1.5 | 5 | 5 | 5 | 5 | 5 | 5 | — |
| | 100 | 1 | 5 | 5 | 5 | 5 | 5 | 5 | — |
| | 50 | 0 | 5 | 4.5 | 5 | 5 | 5 | 5 | — |
| 58 | 200 | 2 | 5 | 5 | 5 | 5 | 5 | 5 | — |
| | 100 | 1.5–2 | 5 | 5 | 5 | 5 | 5 | 5 | — |
| | 50 | 1.5 | 5 | 5 | 5 | 5 | 5 | 5 | — |
| MCPCA | 100 | 2 | 5 | 5 | 5 | 5 | 5 | 5 | ++++ |
| (Comparison) | 50 | 1.5 | 5 | 5 | 4 | 4.5 | 5 | 5 | +++ |

TABLE 1-continued

| Test compound | Rate of application (g/10a) | Herbicidal effect | | | | | | Phytotoxicity to rice |
|---|---|---|---|---|---|---|---|---|
| | | A | B | C | D | E | F | G | |
| | 25 | 1 | 5 | 4.5 | 4 | 4 | 5 | 4 | ++ |
| MT-101 | 400 | 1.5 | 5 | 5 | 5 | 5 | 5 | 5 | ±~+ |
| (Comparison) | 200 | 1 | 5 | 5 | 4.5 | 5 | 5 | 4 | ± |
| | 100 | 0 | 5 | 5 | 4 | 5 | 5 | 3 | ± |
| MCPB | 50 | 0 | 5 | 5 | 5 | 4.5 | 5 | 5 | ++ |
| | 25 | 0 | 4 | 4 | 4.5 | 3 | 4 | 4 | + |
| | 12.5 | 0 | 4 | 4 | 4 | 3 | 4 | 4 | ± |
| Non-treated | | 0 | 0 | 0 | 0 | 0 | 0 | 0 | — |
| 59 | 100 | 1.5-2 | 5 | 5 | 5 | 5 | 5 | 5 | — |
| | 50 | 1 | 5 | 5 | 5 | 5 | 5 | 5 | — |
| | 25 | 0 | 5 | 5 | 5 | 5 | 5 | 5 | — |
| 66 | 200 | 1 | 5 | 5 | 5 | 5 | 5 | 5 | — |
| | 100 | 0 | 4.5 | 4.5 | 5 | 5 | 5 | 5 | — |
| | 50 | 0 | 4.5 | 4.5 | 4.5 | 4.5 | 5 | 4.5 | — |
| 68 | 400 | 0 | 5 | 5 | 5 | 5 | 5 | 5 | — |
| | 200 | 0 | 5 | 5 | 5 | 5 | 5 | 5 | — |
| | 100 | 0 | 5 | 4 | 4.5 | 4.5 | 5 | 4.5 | — |
| 79 | 400 | 1.5 | 5 | 5 | 5 | 5 | 5 | 5 | — |
| | 200 | 0 | 5 | 5 | 5 | 5 | 4.5 | 5 | — |
| | 100 | 0 | 5 | 4.5 | 5 | 5 | 4.5 | 4.5 | — |
| 85 | 400 | 0 | 5 | 4.5 | 5 | 5 | 5 | 5 | — |
| | 200 | 0 | 4.5 | 4.5 | 4.5 | 4.5 | 5 | 5 | — |
| | 100 | 0 | 4 | 4 | 4.5 | 4 | 4.5 | 4 | — |
| 89 | 200 | 0 | 5 | 5 | 5 | 5 | 5 | 5 | — |
| | 100 | 0 | 5 | 4.5 | 5 | 5 | 5 | 5 | — |
| | 50 | 0 | 4.5 | 4 | 4.5 | 4.5 | 5 | 5 | — |
| 92 | 400 | 1 | 5 | 5 | 5 | 5 | 5 | 5 | — |
| | 200 | 0 | 5 | 5 | 5 | 5 | 5 | 4.5 | — |
| | 100 | 0 | 4 | 4 | 5 | 4.5 | 4.5 | 4.5 | — |
| 94 | 400 | 0 | 5 | 5 | 5 | 5 | 5 | 5 | — |
| | 200 | 0 | 5 | 5 | 5 | 5 | 5 | 4.5 | — |
| | 100 | 0 | 5 | 4.5 | 4.5 | 4.5 | 5 | 4 | — |
| 97 | 400 | 0 | 5 | 5 | 5 | 5 | 5 | 5 | — |
| | 200 | 0 | 5 | 4.5 | 5 | 5 | 5 | 4.5 | — |
| | 100 | 0 | 5 | 4 | 4.5 | 5 | 5 | 4 | — |
| 15 | 400 | 1.5 | 5 | 5 | 5 | 5 | 5 | 5 | — |
| | 200 | 0 | 4.5 | 4.5 | 5 | 5 | 5 | 4.5 | — |
| | 100 | 0 | 4 | 4.5 | 5 | 4.5 | 4.5 | 4 | — |
| 29 | 400 | 2 | 5 | 5 | 5 | 5 | 5 | 5 | ± |
| | 200 | 1 | 5 | 5 | 5 | 5 | 5 | 4.5 | ± |
| | 100 | 0 | 5 | 4.5 | 4.5 | 4.5 | 4 | 4 | — |
| 36 | 100 | 1.5 | 5 | 5 | 5 | 5 | 5 | 5 | — |
| | 50 | 1 | 5 | 5 | 5 | 5 | 5 | 5 | — |
| | 25 | 0 | 5 | 5 | 5 | 5 | 4.5 | 4.5 | — |
| 64 | 200 | 5 | 5 | 5 | 5 | 5 | 5 | 4 | — |
| | 100 | 4.5 | 4.5 | 5 | 5 | 5 | 4.5 | 4 | — |
| | 50 | 4 | 4.5 | 4.5 | 5 | 4.5 | 4.5 | 3 | — |
| 107 | 200 | 0 | 5 | 5 | 5 | 5 | 5 | 4 | — |
| | 100 | 0 | 5 | 5 | 5 | 5 | 5 | 4 | — |
| | 50 | 0 | 5 | 5 | 4.5 | 5 | 4.5 | 3 | — |
| 108 | 200 | 1.5 | 5 | 5 | 5 | 5 | 5 | 5 | — |
| | 100 | 1 | 5 | 5 | 5 | 5 | 5 | 5 | — |
| | 50 | 0 | 5 | 5 | 5 | 5 | 5 | 5 | — |
| 109 | 200 | 1.5 | 5 | 5 | 5 | 5 | 5 | 5 | — |
| | 100 | 1 | 5 | 5 | 5 | 5 | 5 | 5 | — |
| | 50 | 0 | 5 | 5 | 5 | 4.5 | 5 | 4.5 | — |
| 110 | 200 | 0 | 5 | 5 | 5 | 5 | 5 | 5 | — |
| | 100 | 0 | 5 | 5 | 5 | 5 | 5 | 4.5 | — |
| | 50 | 0 | 5 | 5 | 5 | 4.5 | 5 | 4 | — |
| 111 | 200 | 1.5 | 5 | 5 | 5 | 5 | 5 | 5 | — |
| | 100 | 0 | 5 | 5 | 5 | 5 | 5 | 4.5 | — |
| | 50 | 0 | 4.5 | 5 | 5 | 5 | 5 | 4.5 | — |

TEST EXAMPLE 2

Treatment of the flooded soil in the plant growth period:

Paddy soil was filed in pots having an inside diameter of 12 cm (area 113 cm²) to provide a simulated paddy. Predetermined amounts of the seeds of *Rotala indica*, *Alisma canaliculatum* and *Scirpus hotarui* were sown and buried to a depth within 1 cm from the soil surface. Two tubers of *Sagittaria pygmaea* and two yound plants of *Eleocharis acicularis* were transplanted, and a set of two closely aligned rice plants in the two-leaf stage was also transplanted in each pot. The soil was then flooded to a water depth of 3 cm, and the plants were grown in a glass greenhouse. Fifteen days after the pot preparation (when *Sagittaria pygmaea* was in the 3.5-4 leaf stage; *Scirpus hotarui* in the 3-leaf stage; *Alisma canaliculatum*, in the 2,5-leaf stage; and rice, in the 3.5-4 leaf stage), each of the test compounds shown in Table 2 was applied at the rates shown in Table 2 in the same way as in Test Example 1. Thirty days after the treatment of the flooded soil in this way, the same examination as in Test Example 1 was made, and the herbicidal effect and phytotoxicity to rice of each of the test compounds were evaluated on the same standards as given in Test Example 1. The results are shown in Table 2.

chloa crus-galli, Monochoria vaginalis, Scirpus hotarui, Cyperus difformis, Rotala indica and Alisma canalicula-

TABLE 2

| Test Compound | Rate of application (g/10a) | Herbicidal effect | | | | | Phytotoxicity to rice (3.5-4 leaf stage) |
|---|---|---|---|---|---|---|---|
| | | C (2-3 leaf stage) | F (2.5 leaf stage) | E (3 leaf stage) | H | G (3.5-4 leaf stage) | |
| 1 | 400 | 5 | 5 | 5 | 5 | 5 | — |
|   | 200 | 5 | 5 | 5 | 5 | 5 | — |
|   | 100 | 5 | 5 | 4.5 | 4 | 5 | — |
| 8 | 200 | 5 | 5 | 5 | 5 | 5 | — |
|   | 100 | 5 | 5 | 5 | 5 | 5 | — |
|   | 50 | 5 | 5 | 5 | 5 | 5 | — |
| 56 | 200 | 5 | 5 | 5 | 5 | 5 | — |
|   | 100 | 5 | 5 | 5 | 5 | 5 | — |
|   | 50 | 5 | 5 | 4.5 | 4 | 5 | — |
| 61 | 200 | 5 | 5 | 5 | 5 | 5 | — |
|   | 100 | 5 | 5 | 5 | 5 | 5 | — |
|   | 50 | 5 | 5 | 5 | 4.5 | 5 | — |
| 55 | 200 | 5 | 5 | 5 | 5 | 5 | — |
|   | 100 | 5 | 5 | 5 | 5 | 5 | — |
|   | 50 | 4.5 | 5 | 4.5 | 4.5 | 4.5 | — |
| 94 | 400 | 5 | 5 | 4.5-5 | 4.5 | 5 | — |
|   | 200 | 4.5 | 4.5 | 4 | 4-4.5 | 5 | — |
|   | 100 | 4 | 4.5 | 4 | 4 | 4 | — |

TEST EXAMPLE 3

Soil from an upland farm was filled in each of rectangular pots with an area of 877.5 cm$^2$, and then treated with compound No. 8 of the invention (250 g/10 ares), MT-101 (250 g/10 ares) and MCPCA (100 g/10 areas), respectively. On the fifth day after the treatment, 25 seeds of Japanese radish were sown in each pot, and the number of days which elapsed until the weight of each radish root (the average weight of 20 radish roots) in each treated pot was less than 50% based on the untreated pot was determined. The results were 10 days for MCPCA, 30 days for MT-101, and 40 days for compound No. 8 of the invention. This demonstrates that the herbicidal compound of the invention has a long-lasting effect.

tum were sown, and tubers and yearling buds of Sagittaria pygmaea, Cyperus serotinus and Eleocharis acicularis were planted. Rice seedlings in the two-leaf stage were transplanted. The pots were placed in a greenhouse, and the plants were grown. On the third day after the sowing when Echinochloa crus-galli sprouted, a water dilution of a wettable powder (prepared as in Formulation Example 2) of each of the test compounds shown in Table 3 was applied at a rate of 12 ml per pot. Then, the plants were grown in the greenhouse, and on the 30th day after the application of the test compound, the herbicidal effect and phytotoxicity to rice were observed and evaluated in the same way as in Test Example 1. The results are shown in Table 3.

TABLE 3

| Test Compound | Rate of application (g/10a) | Herbicidal effect | | | | | | | | Phytotoxicity to rice |
|---|---|---|---|---|---|---|---|---|---|---|
| | | A | B | C | D | E | H | F | G | I | |
| No. 8 + Butachlor | 40 + 10 | 5 | 5 | 5 | 5 | 5 | 5 | 5 | 5 | 5 | — |
|  | 20 + 5 | 5 | 5 | 5 | 5 | 5 | 5 | 5 | 5 | 5 | — |
| No. 61 + Butachlor | 40 + 10 | 5 | 5 | 5 | 5 | 5 | 5 | 5 | 5 | 5 | — |
|  | 20 + 5 | 5 | 5 | 5 | 5 | 5 | 5 | 5 | 5 | 5 | — |
| No. 8 + CG-113 | 40 + 10 | 5 | 5 | 5 | 5 | 5 | 5 | 5 | 5 | 5 | — |
|  | 20 + 5 | 5 | 5 | 5 | 5 | 5 | 5 | 5 | 5 | 5 | — |
| No. 61 + CG-113 | 40 + 10 | 5 | 5 | 5 | 5 | 5 | 5 | 5 | 5 | 5 | — |
|  | 20 + 5 | 5 | 5 | 5 | 5 | 5 | 4.5 | 5 | 5 | 5 | — |
| No. 8 + MY-93 | 50 + 50 | 5 | 5 | 5 | 5 | 5 | 4 | 5 | 5 | 5 | — |
|  | 25 + 25 | 5 | 5 | 5 | 5 | 5 | 3.5 | 5 | 5 | 4.5 | — |
| No. 8 + Molinate | 50 + 50 | 5 | 5 | 5 | 5 | 5 | 5 | 5 | 5 | 5 | — |
|  | 25 + 25 | 5 | 5 | 5 | 5 | 5 | 4.5 | 5 | 5 | 4.5 | — |
| No. 8 + Benthiocarb | 50 + 50 | 5 | 5 | 5 | 5 | 5 | 5 | 5 | 5 | 4.5 | — |
|  | 25 + 25 | 5 | 5 | 5 | 5 | 5 | 5 | 5 | 5 | 4.5 | — |

TEST EXAMPLE 4

Treatment of the flooded soil:

Water was put in each of pots having a diameter of 12 cm and filled with 1 kg of paddy soil (alluvial humus soil) to provide a simultated paddy. Seeds of Echino-

TEST EXAMPLE 5

The plants shown in Table 4 were grown in the same way as in Test Example 1. Fifteen days after sowing (when Echinochloa crus-galli was in the 2-2.5 leaf stage), a wettable powder (prepared as in Formulation Example 2) of each of the test compounds was diluted with water and applied at a rate of 12 ml per pot. The plants were then grown in a greenhouse, and on the 30th day after the treatment of the pots with the test compounds, the herbicidal effect and phytotoxicity to rice were observed and evaluated in accordance with the same standards as in Test Example 1. The results are shown in Table 4.

TABLE 4

| Test Compound | Rate of application (g/10a) | Herbicidal effect | | | | | | | | | Phytotoxicity to rice |
|---|---|---|---|---|---|---|---|---|---|---|---|
| | | A | B | C | D | E | H | F | G | I | |
| No. 8 + Butachlor | 80 + 20 40 + 10 | 5 | 5 | 5 | 5 | 5 | 5 | 5 | 5 | 5 | — |
| No. 8 + CG-113 | 80 + 20 40 + 10 | 5 | 5 | 5 | 5 | 5 | 5 | 5 | 5 | 5 | — |
| Control (non-treated) | — | 0 | 0 | 0 | 0 | 0 | 0 | 0 | 0 | 0 | — |

TEST EXAMPLE 6

Paddy soil was filled in each of concrete pots, 50 cm×50 cm×50 cm in size, to provide a simulated paddy, and predetermined amounts of the seeds of *Echinochloa crus-galli*, *Monochoria vaginalis*, *Scirpus hotarui* and *Alisma canaliculatum* were sown, and tubers of *Sagittaria pygmaea* and *Cyperus serotinus* and yearling buds of *Echinochloa acicularis* were planted. Furthermore, four rice seedlings in the two-leaf stage were transplanted. The pots were placed outdoors (under natural conditions) to grow the plants. On the seventh day after the sowing when *Eleocharis crus-galli* was in the 0.5–0.8 leaf stage, a wettable powder (prepared as in Formulation Example 2) of each of the test compounds shown in Table 5 was diluted with water and applied to each pot at a predetermined rate. The plants were then further grown under proper control. On the 30th day after the treatment of the pots with the test compounds, the weeds and rice plants were pulled out, washed with water, and dried. The weights of these dry plants were measured. The results are shown in Table 5.

Formulation Example 5) of compound No. 8 (4%)+Butachlor (3%), compound No. 8 (4%)+CG-113 (2%), MT-101 (7%)+Butachlor (3%), and MT-101 (7%)+CG-113 (2%) were applied to each pot at a rate of 3 kg/10 ares. Germinated seeds of *Echinochloa crus-galli* were used as an assay plant. On the 20th day after the sowing, the weight of the raw assay plant was measured. The paddy soil used was alluvial humus soil having a humus content of 25.9% and a base substituting capacity of 11.82. The residual period of each test compound (the number of days which elapsed until the percent inhibition of the test compound based on the non-treated pot reached 50%) was shown below.

| Test compounds | Residual period |
|---|---|
| Compound No. 8 + Butachlor | 35 days |
| Compound No. 8 + CG 113 | 30 days |
| MT-101 + Butachlor (comparison) | 25 days |
| MT-101 + CG 113 (comparison) | 25 days |

TEST EXAMPLE 8

A comparative test was conducted to determine the effect of the type of substituents on the benzene ring of the phenoxy group of a phenoxycarboxylic acid anilide-type herbicidal compound and the mode of their substitution on herbicidal activity, phytotoxicity, selectivity between weeds and a gramineous plant, the range of the suitable period of application, a residual effect in the

TABLE 5

| Test Compound | Rate of application (g/10a) | Amount of the remaining weeds (%) based on the non-treated pot | | | | | | | State of growth of rice(*) | |
|---|---|---|---|---|---|---|---|---|---|---|
| | | A | B | H | E | D | G | I | under ground portion | Terrestial portion |
| No. 8 + Butachlor | 40 + 25 | 0 | 0 | 0 | 0 | 0 | 0 | 0 | 100< | 100< |
| | 20 + 25 | 0 | 0 | 7.2 | 0 | 0 | 0 | 0 | 100< | 100< |
| | 40 + 10 | 1.5 | 0 | 0 | 0 | 0 | 0 | 4.6 | 100< | 100< |
| | 20 + 10 | 2.5 | 0 | 9.8 | 0 | 0 | 0 | 10.2 | 100< | 100< |
| No. 8 + CG-113 | 40 + 25 | 0 | 0 | 0 | 0 | 0 | 0 | 0 | 100< | 100< |
| | 20 + 25 | 0 | 0 | 4.2 | 0 | 0 | 0 | 0 | 100< | 100< |
| | 40 + 10 | 0 | 0 | 2 | 0 | 0 | 0 | 5.1 | 100< | 100< |
| | 20 + 10 | 0 | 0 | 8.2 | 0 | 0 | 0 | 8.7 | 100< | 100< |
| Control (non-treated) | — | 100 (20.7 g) | 100 (2.2 g) | 100 (1.2 g) | 100 (4.8 g) | 100 (8.2 g) | 100 (3.6 g) | 100 (9.6 g) | 82.1 | 62.6 |
| Weeds pulled out by hand | — | — | — | — | — | — | — | — | 100 (23.6 g) | 100 (45.2 g) |

(*)Compared with the pot where weeds were removed by hand.

TEST EXAMPLE 7

Test for a residual effect:

Each of pots (1/2000 are) was filled with 1.5 kg of paddy soil, and the soil was flooded to a water depth of 3 cm. On the 45th, 40th, 35th, 30th, 25th, 20th and 10th days and on the day of sowing, granules (prepared as in soil, and reaching of the herbicidal compound in the soil.

Test Compounds

The following compounds were used.

Table 6 given hereinbelow also shows the data given in Japanese Laid-Open Patent Publications Nos.

96323/1978 and 120123/1977 respectively about compound 4 and compound 8 (Runs Nos. 5 and 6).

Run No. 1

Compound No. 8 of the invention represented by formula (I)

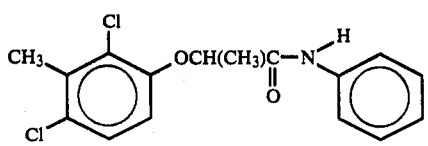

Run No. 2

British Pat. No. 1,041,982 (Chemical Abstracts, vol. 66, 37670g)

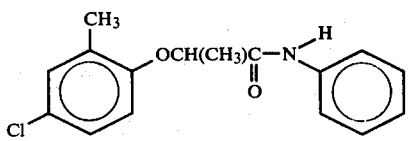

Run No. 3

J. Chem. Soc., 2335 (1961)

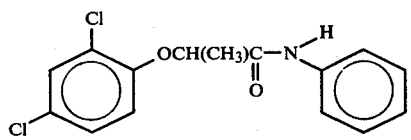

Run No. 4

MCPCA (one component of the mixed herbicide disclosed in Japanese Patent Publication No. 40731/1978)

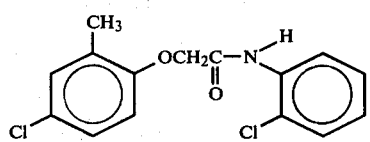

Run No. 5

Japanese Laid-Open Patent Publication No. 96323/1978 (compound 4)

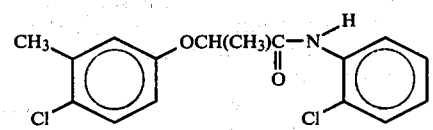

Run No. 6

Japanese Laid-Open Patent No. 120123/1977 (compound 8)

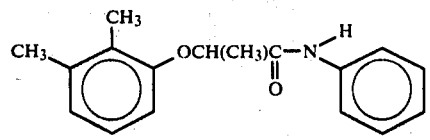

Testing methods (a) Herbicidal effect ($ED_{90}$, g/10 ares)

Treatment with each of the test compounds was effected in accordance with the method described in Test Examples 1 and 2, and the weight of each of the air-dried weeds was measured. The rate of application (g/10 ares) which provided a percent inhibition of about 90% based on the non-treated pot was determined.

(b) Phytotoxicity to rice ($ED_{10}$, g/10 ares)

Treatment with each of the test compounds was effected in accordance with the method described in Test Examples 1 and 2, and the weight of the air-dried roots was measured. The rate of application (g/10 ares) which provided a percent inhibition of about 10% based on the non-treated pot was determined.

(c) Selectivity

The selectivity of each test compound was defined by the quotient of $ED_{10}$ of rice divided by $ED_{90}$ of *Sagittaria pygmaea*.

(d) Residual effect

Paddy soil was put in a rectangular vat with a size of 32.5×27 cm, and treated with each compound No. 8 of the invention and MCPCA (comparison) at a rate of 200 g/10 ares. Seeds of *Alisma canaliculatum* were sown every five days. After fifteen days, the weight of air-dried weeds was measured periodically, and the number of days which elapsed until the percent inhibition based on the non-treated pot reached 50% was determined.

(e) Reaching

Ten ring-like structures each having a height of 1 cm were stacked to form a hollow cylindrical structure, and 750 g of air-dried soil was filled in the cylindrical structure. Two such soil-filled cylindrical structures were provided. Compound No. 8 of the invention was applied to the soil surface of one of the cylindrical structures at a rate of 500 g/10 ares, and MCPCA, to the soil surface of the other at the same dosage. After standing for 24 hours, both were exposed to artificial rainfall at a rate of 30 mm/hr. The cylindrical structures were then allowed to stand for another 24 hours. Each of the cylindrical structures was cut between the adjacent ring structures to provide ten soil columns. Each (1 cm in height) of the columns was put into a tall Petri dish, and seeds of Japanese radish were sown and grown in it. For each cylindrical structure, that column which showed the least growth inhibition was selected, and the length in the original cylindrical structure from the surface of the topmost column to the bottom of the selected columm was measured.

TABLE 6

| | Herbicidal effect $ED_{90}$ (g/10a) |
|---|---|
| Time of | Broad-leaved |

TABLE 6-continued

| Run | Structural formula | treatment | D | weeds E | F | G | H |
|---|---|---|---|---|---|---|---|
| 1 Invention | (2,4-Cl, 3-Me phenoxy)-CH(Me)-CONH-phenyl | Germinating stage | 10 | above 10 | 10 | 20 | 20 | 40 |
| | | Growing stage | 25 | 20 | 25 | 50 | 50 | 50 |
| 2 Comparison | (2-Me, 4-Cl phenoxy)-CH(Me)-CONH-phenyl | Germinating stage | 25 | 25 | 25 | 30 | 100 | |
| | | Growing stage | 25 | 50 | 50 | 50 | 100 | |
| 3 Comparison | (2,4-Cl phenoxy)-CH(Me)-CONH-phenyl | Germinating stage | 25 | 20 | 20 | 20 | 50 | 50 |
| | | Growing stage | 25 | 25 | 50 | 50 | 100 | 50 |
| 4 Comparison | (2-Me, 4-Cl phenoxy)-CH(H)-CONH-(2-Cl phenyl) | Germinating stage | 25 | 20 | 25 | 30 | 50 | |
| | | Growing stage | 25 | 50 | 50 | 50 | 100 | 50 |
| 5 Comparison | (3-Me, 4-Cl phenoxy)-CH(Me)-CONH-(2-Cl phenyl) | Germinating stage | above 100 | above 100 | above 100 | | 100–200 | |
| 6 Comparison | (3-Me, 2-Me phenoxy)-CH(Me)-CONH-phenyl | Germinating stage | 100–200 | 100–200 | | below 200 | below 200 | |

| Run | Phytotoxicity to rice ED$_{10}$ (g/10a) | Selectivity ED$_{10}$/ED$_{90}$ | Range of a suitable period of treatment | Residual effect | Reaching |
|---|---|---|---|---|---|
| 1 Invention | (+3) 100 (+15) 200 | 5 4 | +3~+15 | 35–40 days | 3 cm |
| 2 Comparison | (+3) 30 (+15) 50 | 0.3 0.5 | +20~+30 | | |
| 3 Comparison | (+3) 20 (+15) 50 | 0.4 0.5 | +20~+30 | | |
| 4 Comparison | (+3) 20 (+15) 50 | 0.4 0.5 | +7~+10 | 15–20 days | 4 cm |
| 5 Comparison | | | | | |
| 6 Comparison | | | | | |

What we claim is:

1. A tri- or tetra-substituted phenoxy alkylene- or alkenylene-anilide compound represented by the following formula

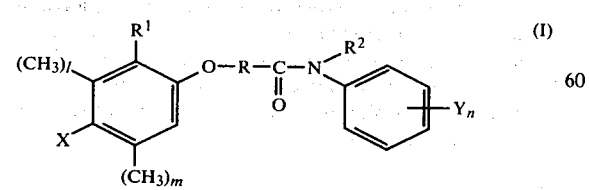

(I)

wherein

R represents a linear or branched lower alkylene or alkenylene group,

R$^1$ represents a methyl group or a halogen atom,

R$^2$ represents a hydrogen atom, or a lower alkyl, lower alkoxy or hyroxyl group, X represents a halogen atom, Y represents a member selected from the class consisting of lower alkyl groups, halogenated lower alkyl groups, lower alkoxy groups, halogen atoms, a nitro group, a cyano group, a hydroxyl group, an amino group, lower alkylamino groups, lower alkanoyloxy groups, lower alkanoylamino group, lower alkylthio groups, lower alkylsulfonyl groups, lower alkanoyl groups, a carboxyl group, lower alkoxycarbonyl groups and lower alkylaminocarbonyl groups, l and m are each 0 or 1 provided that l and m are not zero at the same time, and n is 0 or an integer of 1 to 4 and when n is an integer of 2 to 4, a plurality of Y's are identical or different.

2. The compound of claim 1 wherein in formula (I),
R represents a linear or branched $C_1$-$C_4$ alkylene or $C_2$-$C_4$ alkenylene group,
$R^1$ represents a methyl group or a halogen atom,
$R^2$ represents a hydrogen atom, a $C_1$-$C_4$ alkyl group, a $C_1$-$C_4$ alkoxy group, or a hydroxyl group, and
Y represents a member selected from the class consisting of $C_1$-$C_4$ alkyl groups, halo($C_1$-$C_4$ alkyl) groups having 1 to 4 halogen atoms, $C_1$-$C_4$ alkoxy groups, halogen atoms, a nitro group, a cyano group, a hydroxyl group, an amino group, mono- or di-($C_1$-$C_4$ alkyl) amino groups, $C_2$-$C_4$ alkanoyloxy groups, $C_2$-$C_4$ alkanoylamino groups, $C_1$-$C_4$ alkylthio groups, $C_1$-$C_4$ alkylsulfonyl groups, $C_2$-$C_4$ alkanoyl groups, $C_1$-$C_4$ alkoxy-carbonyl groups and mono- or di-($C_1$-$C_4$ alkyl)-aminocarbonyl groups.

3. The compound of claim 1 wherein in formula (I),
R represents —$CH_2$— or —$CH(CH_3)$—,
$R^1$ represents a halogen atom,
$R^2$ represents a hydrogen atom, a $C_1$-$C_4$ alkyl group, a $C_1$-$C_4$ alkoxy group, or a hydroxyl group,
Y represents a member selected from the class consisting of $C_1$-$C_4$ alkyl groups, halo-($C_1$-$C_4$ alkyl) groups having 1 to 4 carbon atoms, $C_1$-$C_4$ alkoxy groups, halogen atoms, a nitro group, a cyano group, a hydroxyl group, an amino group, mono- or di-($C_1$-$C_4$ alkyl) amino groups, $C_2$-$C_4$ alkanoyloxy groups, $C_2$-$C_4$ alkanoylamino groups, $C_1$-$C_4$ alkylthio groups, $C_1$-$C_4$ alkylsulfonyl groups, $C_2$-$C_4$ alkanoyl groups, $C_1$-$C_4$ alkoxy-carbonyl groups, and mono- or di-($C_1$-$C_4$ alkyl)-aminocarbonyl groups, and
l and m are each 0 or 1 provided that l and m are not zero at the same time, and
n is 0 or an integer of 1 to 3 and when n is an integer of 2 to 3, a plurality of Y's are identical or different.

4. A herbicidal composition (1) consisting essentially of about 0.1 to about 99.0% by weight, based on the weight of the composition, of a tri-or tetra-substituted phenoxy alkylene-or alkenylene-anilide compound represented by the following formula

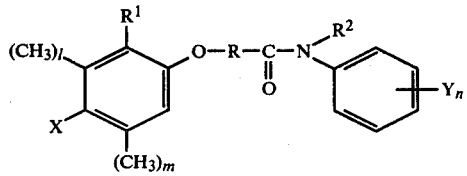

wherein
R represents a linear or branched lower alkylene or alkenylene group,
$R^1$ represents a methyl group or a halogen atom,
$R^2$ represents a hydrogen atom, or a lower alkyl, lower alkoxy or hydroxyl group,
X represents a halogen atom, Y represents a member selected from the group consisting of lower alkyl groups, halogenated lower alkyl groups, lower alkoxy groups, halogen atoms, a nitro group, a cyano group, a hydroxyl group, an amino group, lower alkylamino groups, lower alkanoyloxy groups, lower alkanoylamino groups, lower alkylthio groups, lower alkylsulfonyl groups, lower alkanoyl groups, a carboxyl group, lower alkoxycarbonyl groups and lower alkylaminocarbonyl groups, l and m are each 0 or 1 provided that l and m are not zero at the same time, and
n is 0 or an integer of 1 to 4 and when n is an integer of 2 to 4, a plurality of Y's are identical or different, and (2) a liquid or solid diluent or carrier.

5. the herbicidal composition of claim 4 wherein in formula (I),
R represents a linear or branched $C_1$-$C_4$ alkylene or $C_2$-$C_4$ alkenylene group,
$R^1$ represents a methyl group or a halogen atom,
$R^2$ represents a hydrogen atom, a $C_1$-$C_4$ alkyl group, a $C_1$-$C_4$ alkoxy group, or a hydroxyl group, and
Y represents a member selected from the class consisting of $C_1$-$C_4$ alkyl groups, halo-($C_1$-$C_4$ alkyl) groups having 1 to 4 halogen atoms, $C_1$-$C_4$ alkoxy groups, halogen atoms, a nitro group, a cyano group, a hydroxyl group, an amino group, mono- or di-($C_1$-$C_4$ alkyl) amino groups, $C_2$-$C_4$ alkanoyloxy groups, $C_2$-$C_4$ alkanoylamino groups, $C_1$-$C_4$ alkylthio groups, $C_1$-$C_4$ alkylsulfonyl groups, $C_2$-$C_4$ alkanoyl groups, $C_1$-$C_4$ alkoxy-carbonyl groups and mono- or di-($C_1$-$C_4$ alkyl)-aminocarbonyl groups.

6. The herbicidal composition of claim 4 wherein in formula (I),
R represents —$CH_2$— or —$CH(CH_3)$—,
$R^1$ represents a halogen atom,
$R^2$ represents a hydrogen atom, a $C_1$-$C_4$ alkyl group, a $C_1$-$C_4$ alkoxy group, or a hydroxyl group,
Y represents a member selected from the class consisting of $C_1$-$C_4$ alkyl groups, halo-($C_1$-$C_4$ alkyl) groups having 1 to 4 halogen atoms, $C_1$-$C_4$ alkoxy groups, halogen atoms, a nitro group, a cyano group, a hydroxyl group, an amino group, mono- or di-($C_1$-$C_4$ alkyl) amino groups, $C_2$-$C_4$ alkanoyloxy groups, $C_2$-$C_4$ alkanoylamino groups, $C_1$-$C_4$ alkylthio groups, $C_1$-$C_4$ alkylsulfonyl groups, $C_2$-$C_4$ alkanoyl groups, $C_1$-$C_4$ alkoxy-carbonyl groups, and mono- or di-($C_1$-$C_4$ alkyl)-aminocarbonyl groups, and
l and m are each 0 or 1 provided that l and m are not zero at the same time, and
n is 0 or an integer of 1 to 3 and when n is an integer of 2 to 3, a plurality of Y's are identical or different.

7. The herbicidal composition of claim 4 which further comprises another herbicidally active compound.

8. The herbicidal composition of claim 7 wherein the other herbicidally active compound is at least one compound selected from the group consisting of α-chloro-2',6'-diethyl-N-(butoxymethyl)acetanilide, α-chloro-2',6'-diethyl-N-(propoxyethyl)acetanilide, S-ethyl-N,N-hexamethylenethiol carbamate, S-(4-chlorobenzyl)-N,N-diethylthiol carbamate, S-(α,α-dimethylbenzyl)-N,N-pentamethylenethiol carbamate, O,O-diisopropyl-S-(2-benzenesulfonylaminoethyl)phosphorodithioate, O-ethyl-0-(2-nitro-5-methylphenyl)-N-sec.-butylphosphoramidothioate, O,O-diisopropyl-S-(2-methylpiperidin-1-yl-carbonylmethyl)phosphorodithioate, and 0,0-diphenyl-S-(2-methylpiperidin-1-yl-carbonylmethyl)-phosphorodithioate.

9. A method for controlling the growth of the undesired vegetation *Cyperus difformis, Cyperus Serotinus, Monochoria Vaginalis, Rotala indica, Lindernia Pyxidaria, Dopatrium junceum, Labelia radicans, Elipta alba, Eleocharis acicularis, Scirpus hotarui, Sagittaria Pygmaea, Alisma Canaliculatum* or *Oenanthe javanica* which comprises applying an effective amount of the compound of claim 1 to the locus to be protected from said undesired vegetation.

10. The method of claim 9 wherein the amount of the compound to be applied is about 1 to about 1000 g per 10 ares of said locus.

* * * * *